(12) United States Patent
Lee et al.

(10) Patent No.: US 6,566,393 B1
(45) Date of Patent: May 20, 2003

(54) ETOPOSIDE ANALOGS AND METHODS OF USE THEREOF

(75) Inventors: Kuo-Hsiung Lee, Chapel Hill, NC (US); Zhiyan Xiao, Chapel Hill, NC (US); Kenneth F. Bastow, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/177,147

(22) Filed: Jun. 21, 2002

(51) Int. Cl.⁷ .................. A61K 31/335; A61K 31/38

(52) U.S. Cl. .................. 514/463; 514/431; 549/10; 549/298; 549/432; 549/433

(58) Field of Search ............... 549/10, 298, 432, 549/433; 514/431, 463

(56) References Cited

U.S. PATENT DOCUMENTS

| | | | |
|---|---|---|---|
| 4,958,010 A | 9/1990 | Kadow et al. |
| 5,132,322 A | 7/1992 | Lee et al. |
| 5,300,500 A | 4/1994 | Lee et al. |
| 5,332,811 A | 7/1994 | Lee et al. |
| 5,338,867 A | 8/1994 | Choy et al. |
| 5,541,223 A | 7/1996 | Lee et al. |
| 5,571,914 A | 11/1996 | Terada et al. |
| 6,281,198 B1 | 8/2001 | Monneret et al. |

*Primary Examiner*—Amelia Owens
(74) *Attorney, Agent, or Firm*—Myers Bigel Sibley & Sajovec

(57) ABSTRACT

Etoposide analogs such as 4'-O-demethyl-4β-[4"-(methyl-L-tyrosine-N-carbonyl)-anilino]-4-desoxy-podophyllotoxin (12) and 4'-O-demethyl-4β-[4"-(methyl-L-tryptophan-N-carbonyl)-anilino]-4-desoxypodophyllotoxin (13) are described, along with pharmaceutical formulations containing the same, methods of use thereof, and intermediates and methods of making the same.

25 Claims, No Drawings

ETOPOSIDE ANALOGS AND METHODS OF USE THEREOF

STATEMENT OF FEDERAL SUPPORT

This invention was made with government support under NIH grant CA 17625-24. The Government has certain rights to this invention.

FIELD OF THE INVENTION

The present invention concerns etoposide or podophyllotoxin analogs such as 4-beta-[(4"-benzamido)-amino]-epipodophyllotoxins, pharmaceutical formulations containing the same, and the use thereof to treat cancer.

BACKGROUND OF THE INVENTION

Etoposide (1) and Teniposide (2) are semisynthetic glucosidic cyclic acetals of podophyllotoxin (3) currently used in the chemotherapy for various types of cancer

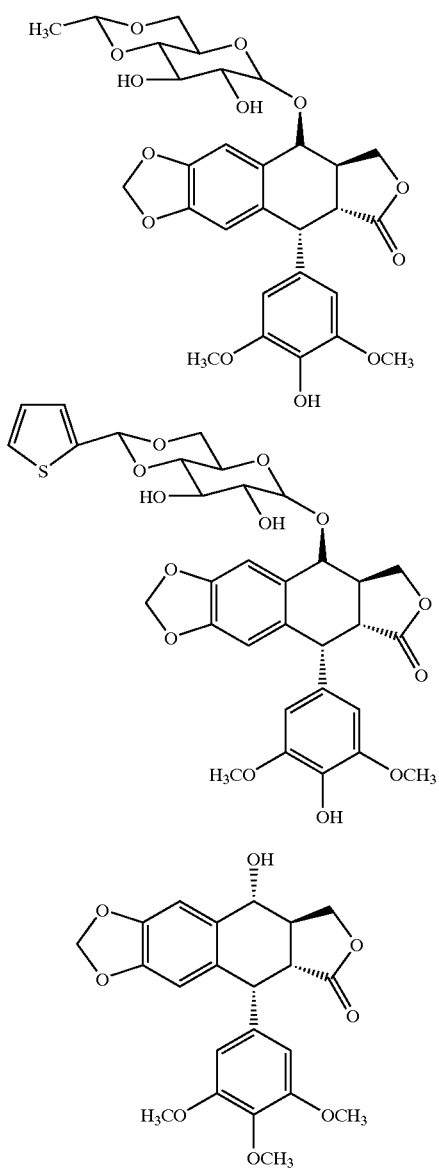

(Jardine. (1980) *Anticancer Agents Based on Natural Products Models;* Academic Press: New York, p. 319, Issell. (1982) *Cancer Chemother. Pharmacol.* 7:73). Another epipodophyllotoxin derivative, GL-331, has been developed and tested in phase II clinical trials against various cancers (Lee et al. (1995) *Food and Drug Analysis.* 3:209). Interestingly, although podophyllotoxin inhibits the assembly of microtubules, the primary action mode of its 4β-congeners, the epipodophyllotoxins, is to inhibit the catalytic activity of topoisomerase II by stabilizing the covalent topoisomerase II-DNA cleavable complex, cause DNA strands breaking and eventually lead to cell death (Osheroff et al. (1991) *BioEssays* 13:269, Alton & Harris (1993) *Br. J. Haematol.* 85:241–245, Cho et al. (1996) *J. Med. Chem.* 39:1383–1395, MacDonald et al. (1991) *DNA Topoisomerase in Cancer;* Oxford University Press: New York, p. 119).

U.S. Pat. No. 5,300,500 to Lee et al. describes a podophyllotoxin analog of formula 4-V as follows:

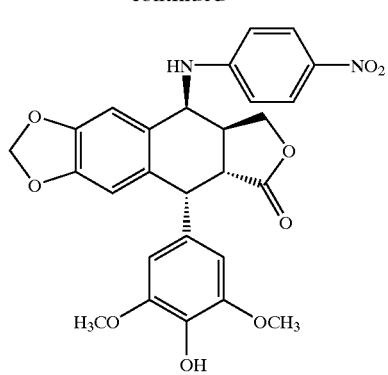

4-V

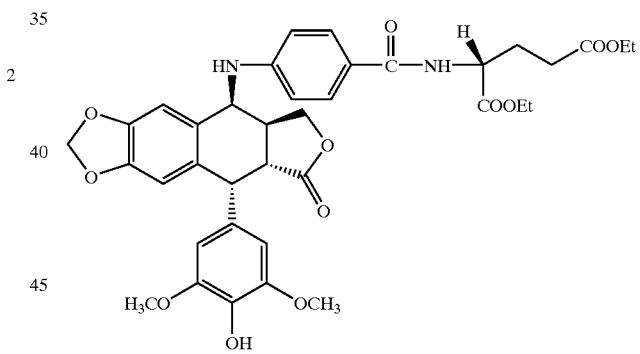

There remains a need for new etoposide analogs with anticancer and antitumor activity.

SUMMARY OF THE INVENTION

A first aspect of the present invention is a compound according to Formula I:

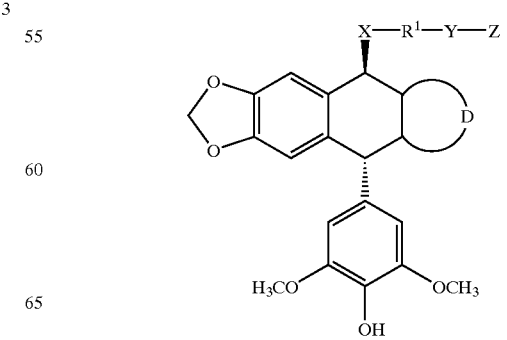

I wherein:
X is a linking group selected from the group consisting of —O—, —S—, —NH—, —CO—, —CH=N—, or CH$_2$NH—, and in one preferred embodiment is —NH—; R$^1$ is a covalent linkage between X and Y, or is loweralkyl, loweralkenyl, or phenyl, and when phenyl is unsubstituted or is substituted from one to four times with loweralkyl, hydroxy, alkoxyl, alkylogen, or alkylamino, alkyoxycarbonyl, amino, halogen, nitro, or nitrile, and in one preferred embodiment R$^1$ is phenyl;

Y is —NHCO— or —CONH—;

Z is —CHR$_2$—(CH$_2$)$_n$R$_3$, where n is 0 to 2 and R$_2$ is —COOH, —NH$_2$, —COOR$_{31}$ where R$_{31}$ is loweralkyl, COOCH$_2$Ph, or —NHCOOCH$_2$Ph ("Ph" meaning phenyl);

R$_3$ is a lower alkyl, loweralkenyl or aryl, which may be unsubstituted or substituted one or more times with loweralkyl, loweralkenyl, or hydroxy, alkoxyl, alkylamino, thioalkyl, hydroxycarbonyl, guanidino, or amido, and in one preferred embodiment R$^3$ is phenyl, indolyl, imidazolyl, pyridyl, pyrimidyl, or benzamidazolyl; and D is selected from the group consisting of —CH$_2$OC(=O)—; —CH$_2$OC(=CH$_2$)—; —CH$_2$CH$_2$C(=O)—; —CH$_2$OC(=S)—; —CH$_2$OCH$_2$—; —CH$_2$OCH(—OH)—; —CH$_2$OCH(OCH$_3$)—; —CH$_2$CH$_2$C(—NR$_{12}$)— where R$_{12}$ is loweralkyl; —C(=O)CH$_2$C(O)—; —CH$_2$OS(=O)(=O)OCH$_2$—; and —CH$_2$OS(=O)OCH$_2$—;

or a pharmaceutically acceptable salt thereof.

A particular embodiment of the foregoing is a compound having the structure of Formula II:

II

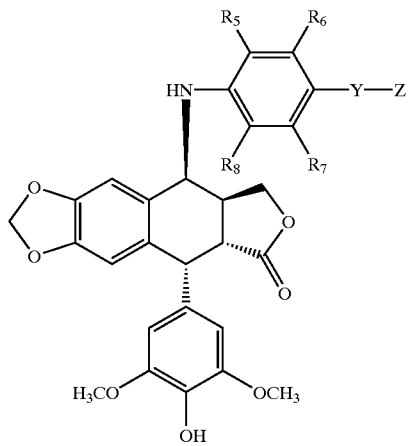

wherein:
Y is an —NHCO— or —CONH— linking group;

Z is —CHR$_2$—(CH$_2$)$_n$R$_3$, where n is 0 to 2 and R$_2$ is —COOH, —NH$_2$, —COOCH$_3$, COOCH$_2$Ph, or —NHCOOCH$_2$Ph;

R$_3$ is a lower alkyl, loweralkenyl or phenyl; and

R$_5$, R$_6$, R$_7$, and R$_8$ are each independently selected from the group consisting of H, loweralkyl, hydroxy, alkoxyl, alkylogen, or alkylamino, alkyoxycarbonyl, amino, halogen, nitro, and nitrile;

or a pharmaceutically acceptable salt thereof.

A further aspect of the present invention is a pharmaceutical formulation comprising a compound as described above in a pharmaceutically acceptable carrier (e.g.,an aqueous carrier).

A still further aspect of the present invention is a method of treating a cancer, comprising administering to a human or animal subject in need thereof a treatment effective amount (e.g., an amount effective to treat, slow the progression of, etc.) of a compound as described above. Examples of cancers that may be treated include, but are not limited to, skin cancer, lung cancer including small cell lung cancer and non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

DETAILED DESCRIPTION OF THE INVENTION

The present invention will now be described more fully hereinafter with reference to the accompanying figures, which further illustrate the invention described herein. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

The term "alkyl" or "loweralkyl" as used herein refers to C1 to C4, C6 or C8 alkyl, which may be linear or branched and saturated or unsaturated.

"Cycloalkyl" is specified as such herein, and is typically C3, C4 or C5 to C6 or C8 cycloalkyl.

"Alkenyl" or "loweralkenyl" as used herein likewise refers to C1 to C4 alkenyl, and alkoxy or loweralkoxy as used herein likewise refers to C1 to C4 alkoxy.

"Alkoxy" as used herein refers to linear or branched, saturated or unsaturated oxo-hydrocarbon chains, including for example methoxy, ethoxy, propoxy, isopropoxy, butoxy, and t-butoxy.

The term "aryl" as used herein refers to C3 to C10 cyclic aromatic groups such as phenyl, naphthyl, and the like, and includes substituted aryl groups such as tolyl.

"Halo" as used herein refers to any halogen group, such as chloro, fluoro, bromo, or iodo.

The term "hydroxyalkyl" as used herein refers to C1 to C4 linear or branched hydroxy-substituted alkyl, i.e., —CH$_2$OH, —(CH$_2$)$_2$OH, etc.

The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc.

The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

The term "alkylenedioxy" refers to a group of the general formula —OR'O—, —OR'OR'—, or —R'OR'OR'— where each R' is independently alkyl.

"Treat" or "treating" as used herein refers to any type of treatment that imparts a benefit to a patient afflicted with a disease, including improvement in the condition of the patient (e.g., in-one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

The present invention is concerned primarily with the treatment of human subjects, but may also be employed for the treatment of other animal subjects (i.e., mammals, avians) for veterinary purposes. Mammals are preferred, with humans being particularly preferred.

A. Active Compounds

Active compounds of the present invention may be produced by the procedures described herein or variations thereof which will be apparent to those skilled in the art. Novel intermediates useful for producing the active compounds described herein are also an aspect of the present invention, as are novel methods useful for producing such intermediates and active compounds.

Intermediates: One example of an intermediate which may be used to carry out the methods of synthesis described below is as follows:

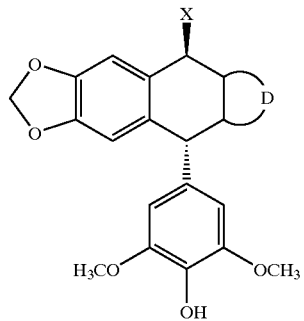

where X is a linking group selected from the group consisting of —CH=N—, or —CH$_2$NH—; and D is selected from the group consisting of —CH$_2$OC(=CH$_2$)—; —CH$_2$CH$_2$C(=O)—; —CH$_2$OC(=S)—; —CH$_2$CH$_2$C(—NR$_{12}$)— where R$_{12}$ is loweralkyl; —C(=O)CH$_2$C(O)—; —CH$_2$OS(=O)(=O)OCH$_2$—.

Synthetic Methods: Synthetic methods for X derivations: When X is —S— (Z. G. Wang et al. (1992) *Yaoxue Xuebao.* 27: 656), —NH— (K. H. Lee et al. (1989) *J. Nat. Prod.* 52:606), or —CO— (Z. X. Chen et al. (2000) *Chinese Chemical Letters.*11:505), published synthetic procedures are applied.

When X is —CH=N— or —CH$_2$NH—, the following synthetic methods may be applied:

—CH=N— :

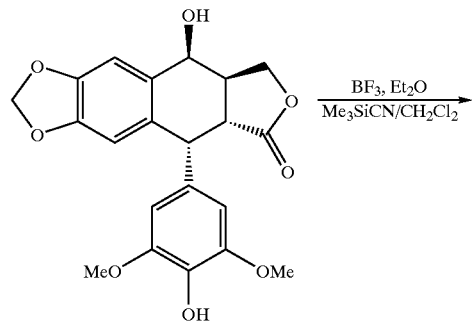

-continued

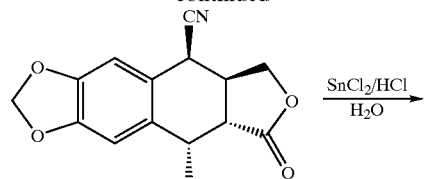

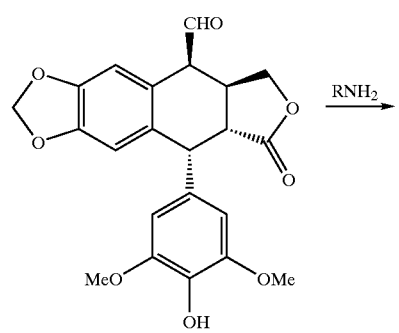

—CH$_2$NH— :

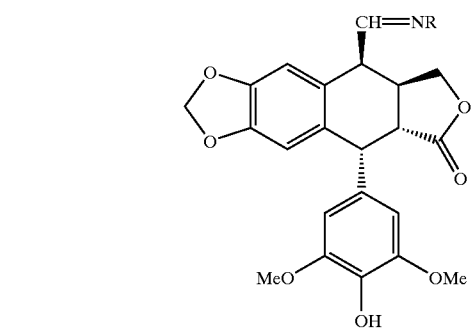

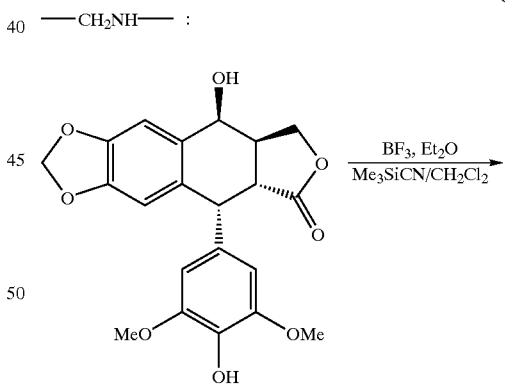

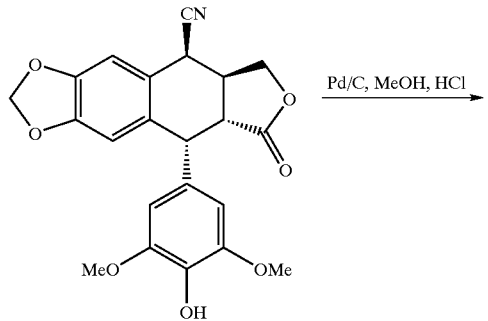

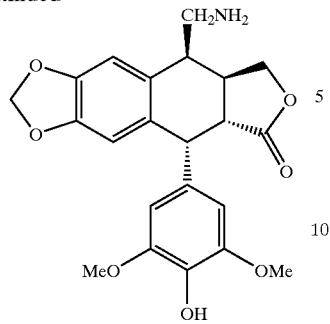
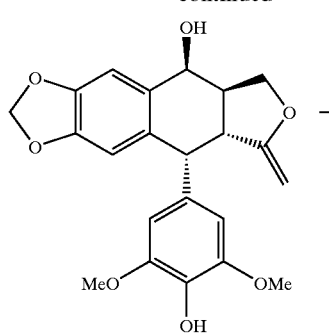
General Synthetic method for C4 side chain extension: Using conjugation agents: 1,3-dicyclohexylcarbodiimide (DCC) and 4-(dimethylamino) pyridine (DMAP)
Synthetic methods for D derivations: When D is —$CH_2OC(=CH_2)$—:
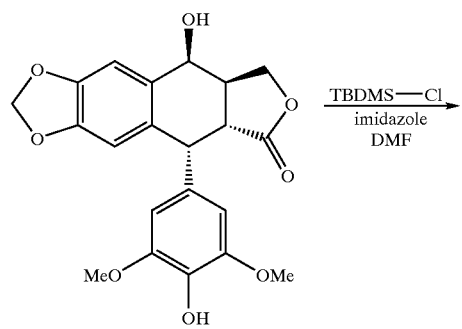
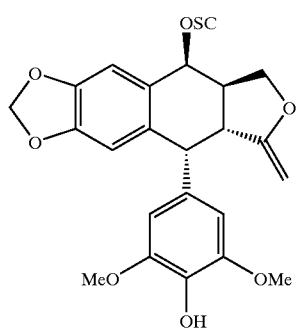
OSC = "Optimized Side Chains"
When D is —$CH_2CH_2C(=O)$— or —$CH_2CH_2C(=NR)$—:
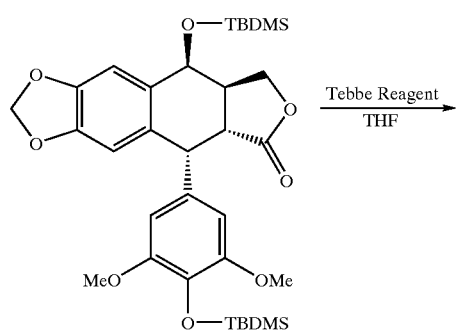
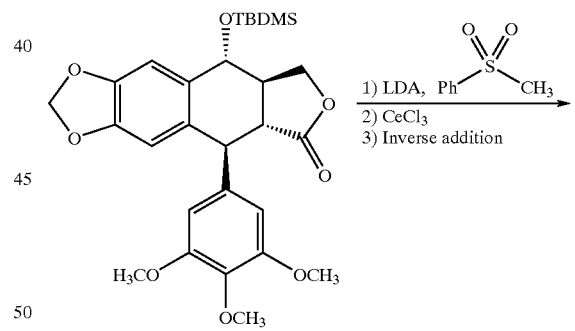
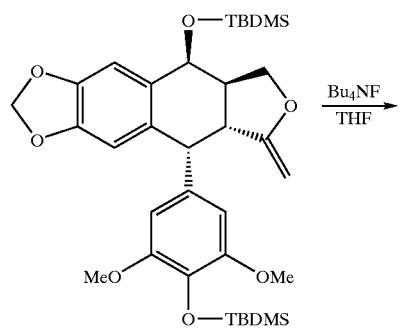
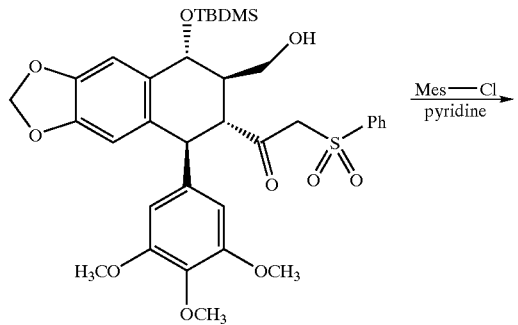

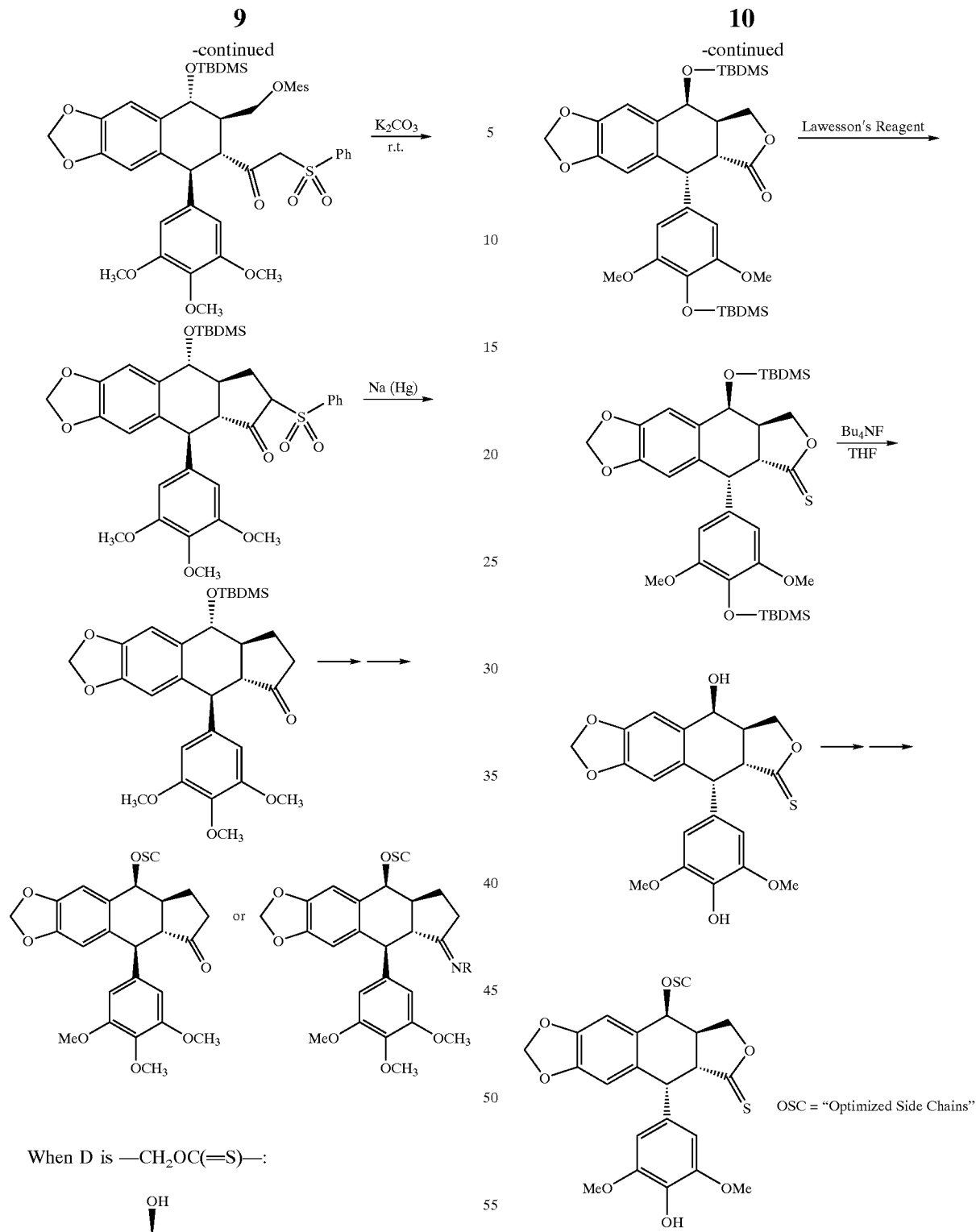
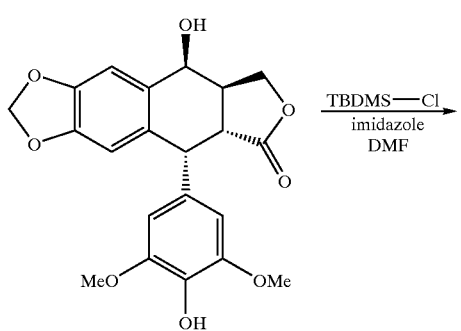
When D is —CH₂OC(=S)—:
When D is —CH$_2$OCH$_2$—, —CH$_2$OCH(—OH)—, or —CH$_2$OCH(OCH$_3$)—: The procedures detailed in X. M. Zhou et al. (1994) *J. Med. Chem.* 37:287 are followed.
Examples of active compounds of the present invention that can be produced by the procedures described above include, but are not limited to:

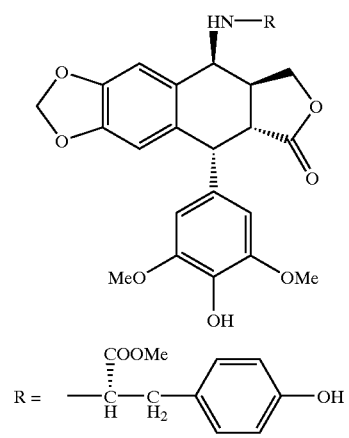
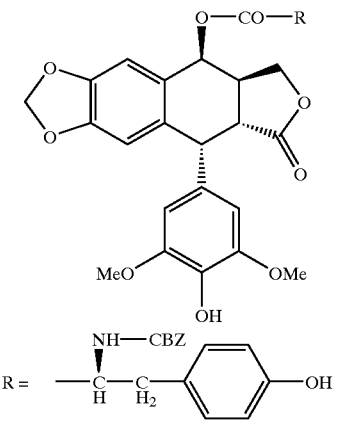
4'-O-demethyl-4β-(L-tyrosyl-C-amino)-4-desoxy-podophyllotoxin
4'-O-demethyl-4β-(methyl L-tyrosyl-N)-4desoxy-podophyllotoxin
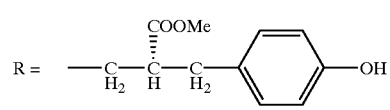
4'-O-demethyl-4β-(N-CBZ-L-tyrosyl-C)-4podophyllol
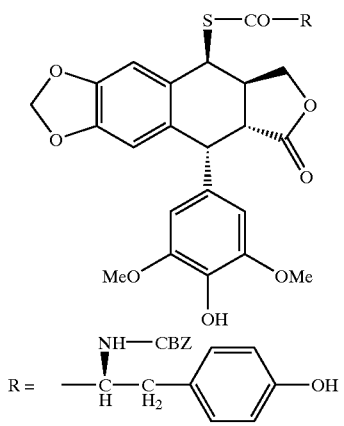
4'-O-demethyl-4β-{[(4"-hydroxyl-benzenepropanoic methyl ester)-α]-methylamino}-4-desoxy-podophyllotoxin
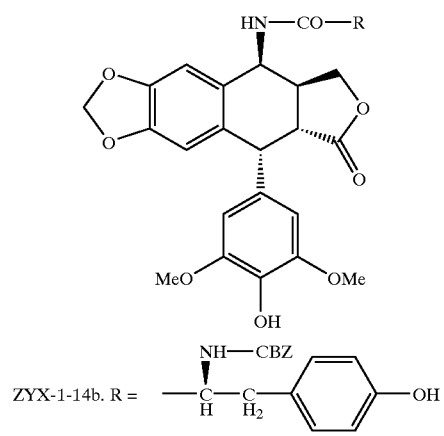
4'-O-demethyl-4β-(N-CBZ-L-tyrosyl-C)-4-thio-podophyllol
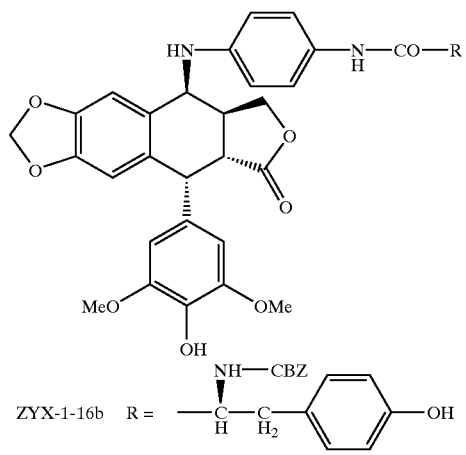
4'-O-demethyl-4β-(N-CBZ-L-tyrosyl-C-amino)-4-desoxy-podophyllotoxin
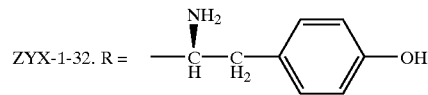

13

4'-O-demethyl-4β-{[4"-(N-CBZ-L-tyrosyl-C-amino)]-anilino}-4-desoxypodophyllotoxin

ZYX-1-19b. R = —CH(COOMe)—CH₂—C₆H₄—OH

4'-O-demethyl-4β-{[4"-(methyl L-tyrosyl-N-carbonyl)]-anilino}-4-desoxy-podophyllotoxin

ZYX-1-40. R = —CH(COOMe)—CH₂-(1H-indol-3-yl)

4'-O-demethyl-4β-{[4"-(methyl L-tryptophanyl-N-carbonyl)]-anilino}-4-desoxypodophyllotoxin

ZYX-2-53b. R = —CH(COOMe)—CH₂-(imidazol-4-yl)

4'-O-demethyl-4β-{[4"-(methyl L-histidyl-N-carbonyl)]-anilino}-4-desoxypodophyllotoxin

ZYX-2-55. R = —CH(COOH)—CH₂-(1H-indol-3-yl)

4'-O-demethyl-4β-{[4"-(L-tryptophanyl-N-carbonyl)]-anilino}-4-desoxypodophyllotoxin

ZYX-2-58a. R = —CH(COOMe)—CH₂-(1H-indol-3-yl)

14

4'-O-demethyl-4β-{[4"-(methyl D-tryptophanyl-N-carbonyl)]-anilino}-4-desoxypodophyllotoxin

ZYX-2-42a. R = —CH₂—COOCH₂Ph

4'-O-demethyl-4β-(benzyl glycyl-N-carbonyl)-4-desoxypodophyllotoxin

ZYX-2-42b. R = —CH(COOMe)—CH₂-(1H-indol-3-yl)

4'-O-demethyl-4β-(benzyl L-tryptophanyl-N-carbonyl)-4-desoxypodophyllotoxin

R = —CH(COOMe)—CH₂—C₆H₄—OH

4'-O-demethyl-4β-(benzyl L-tyrosyl-N-carbonyl)-4-desoxypodophyllotoxin

R = —CH₂NH—CBZ

4'-O-demethyl-4β-(N-CBZ-glycyl-C-methylamino)-4-desoxy-podophyllotoxin

R = —CH(NH—CBZ)—CH₂—C₆H₄—OH

15

4'-O-demethyl-4β-(N-CBZ-L-tyrosyl-C-methylamino)-4-desoxy-podophyllotoxin

4'-O-demethyl-4β-(N-CBZ-L-trptophanyl-C-methylamino)-4-desoxy-podophyllotoxin

4'-O-demethyl-4β-(methyl L-tyrosyl-N-methylene)-4-desoxy-podophyllotoxin

16

4'-O-demethyl-4β-(N-CBZ-L-tyrosyl-C-amino)-4-desoxy-13-methylene-podophyllotoxin

4'-O-demethyl-4β-(methyl L-tyrosyl-N-carbonyl)-4-desoxy-13-methylene-podophyllotoxin

4'-O-demethyl-4β-(N-CBZ-L-tyrosyl-C-methylamino)-4-desoxy-13-methylene-podophyllotoxin

17

4'-O-demethyl-4β-(N-CBZ-L-tyrosyl-C-amino)-4-desoxy-[2α,3β]-cyclopentan-13-one-podophyllotoxin

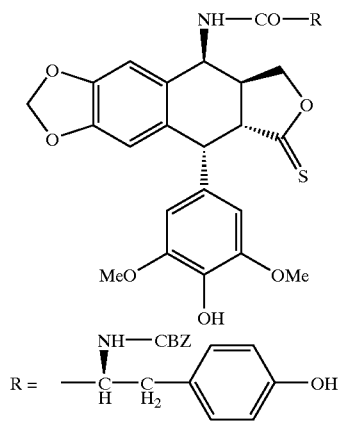

4'-O-demethyl-4β-(N-CBZ-L-tyrosyl-C-amino)-4-desoxy-13-thio-podophyllotoxin

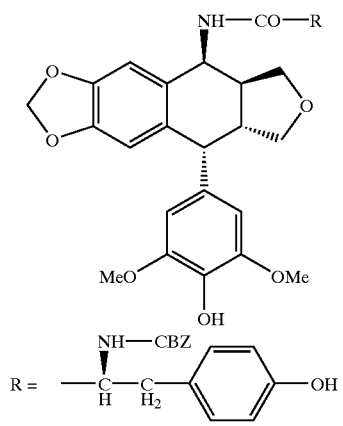

4'-O-demethyl-4β-(N-CBZ-L-tyrosyl-C-amino)-4,13-desoxy-podophyllotoxin

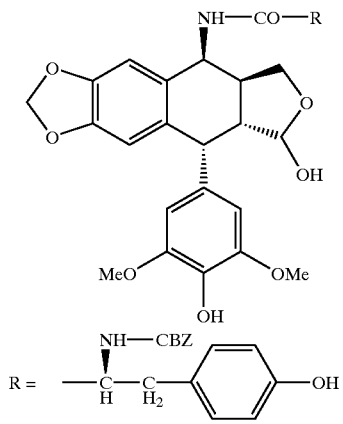

18

4'-O-demethyl-4β-(N-CBZ-L-tyrosyl-C-amino)-4-desoxy-13-hydroxyl-podophyllotoxin

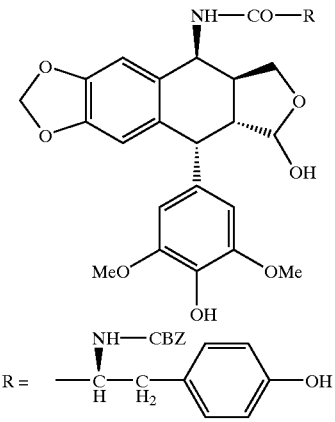

4'-O-demethyl-4β-(N-CBZ-L-tyrosyl-C-amino)-4-desoxy-13-methyl ether-podophyllotoxin

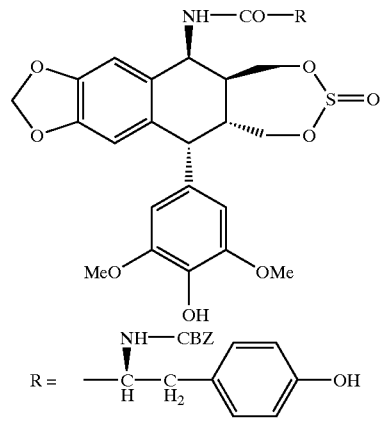

4'-O-demethyl-4β-(N-CBZ-L-tyrosyl-C-amino)-4-desoxy-11,13-O,O'-cyclosulfite-podophyllotoxin

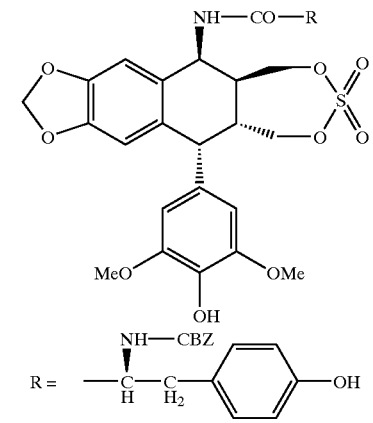

4'-O-demethyl-4β-(N-CBZ-L-tyrosyl-C-amino)-4-desoxy-11,13-O,O'-cyclosulfate-podophyllotoxin B. Formulations and Pharmaceutically Acceptable Salts The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

The compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3:318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

C. Methods of Use

In addition to the compounds of the formulas described herein, the present invention also provides useful therapeutic methods. For example, the present invention provides a method of inducing cytotoxicity against tumor cells, or treating a cancer or tumor in a subject in need thereof.

Cancer cells which may be inhibited include cells from skin cancer, small cell lung cancer, non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formulae described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLE 1

Experimental. The compounds 10–14 were synthesized from podophyllotoxin (3) as outlined in Scheme 1 according to previous published methods. 4'-demethyl-epipodophyllotoxin (DMEP, 5) was synthesized from podophyllotoxin stereoselectively using the methanesulphonic acid/sodium iodide reagents (Kamal et al. (2000) *Bioorg. Med. Chem. Lett.* 10:2059) followed by nucleophilic substitution with water. This intermediate was subjected to nucleophilic displacement by sodium azide or 4-nitroalinine to provide intermediates 4 and 6, which underwent Pd-C catalyzed hydrogenation to generate amines 7 and 8. Compounds 10 and 11 were synthesized from condensation of 7 and 8 respectively with the corresponding carbonic acid, L-N-CBZ tyrosine, by employing reagent dicyclohexylcarbodiimide (DCC). Nuclceophilic displacement of the $C_4$ hydroxyl of 5 with 4-amino benzoic acid gave compound 9, which was condensed with L-tyrosine methyl ester, L-tryptophan methyl ester or 4-(benzimidazol-2-yl)-aniline to provide compounds 12–14 respectively.

All melting points were taken on Fisher-Johns and Mel-Temp II melting point instruments and are uncorrected. IR spectra were recorded on a Perkin-Elmer 1320 spectrophotometer. $^1$H NMR spectra were obtained using Bruker AC-300 and WM 250 NMR spectrometers with TMS as the internal standard. All chemical shifts are reported in ppm. FABMS and HRFABMS spectral analyses were determined on a JOEL HX-110 instrument. Analytical thin-layer chromatography (TLC) was carried out on Merck precoated aluminum silica gel sheets (Kieselgel 60 F-254). Optical rotations were measured with a JASCO DIP-1000 polarimeter. All target compounds were characterized by $^1$H and IR spectral analyses and MS analyses.

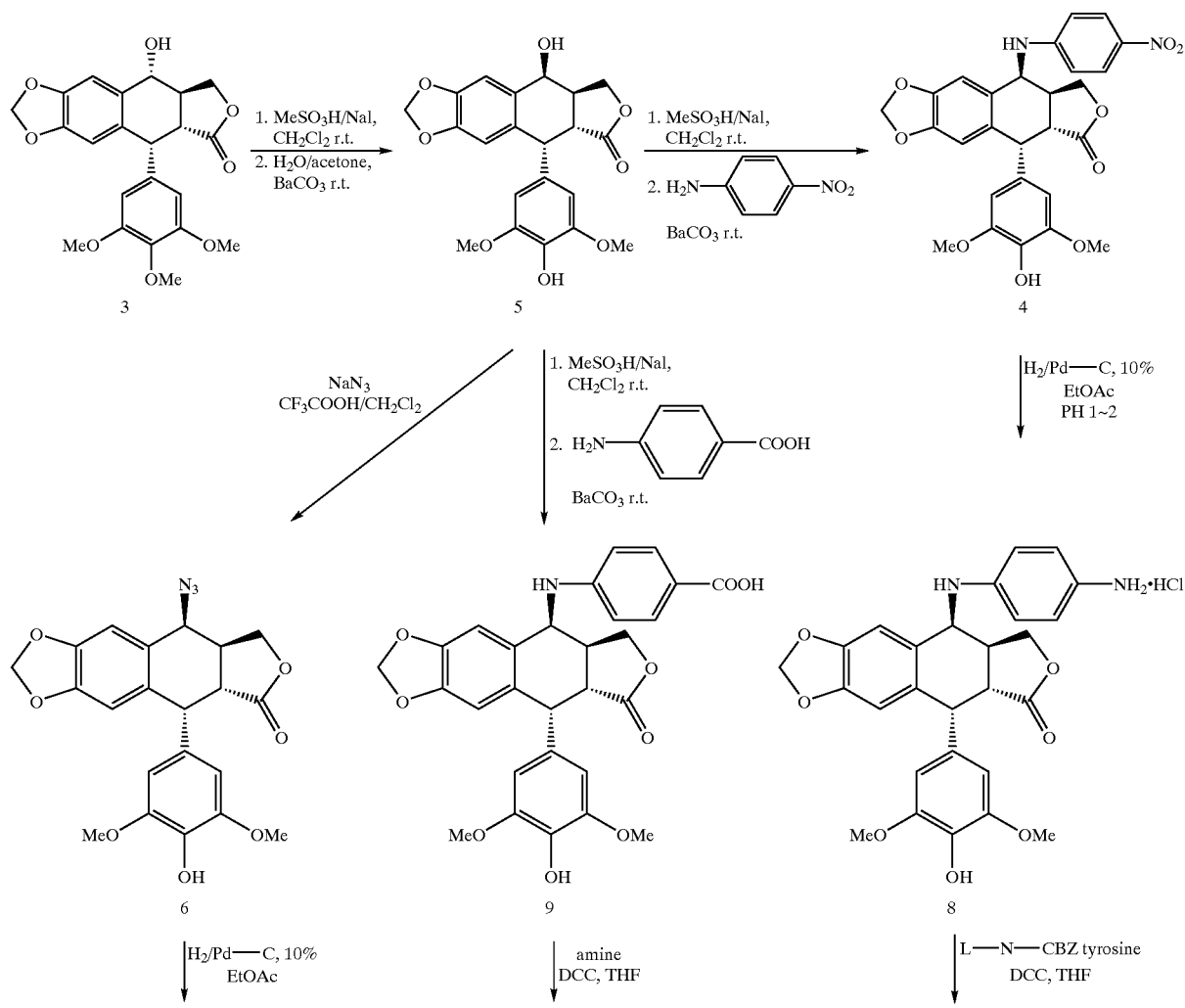

Scheme 1

-continued

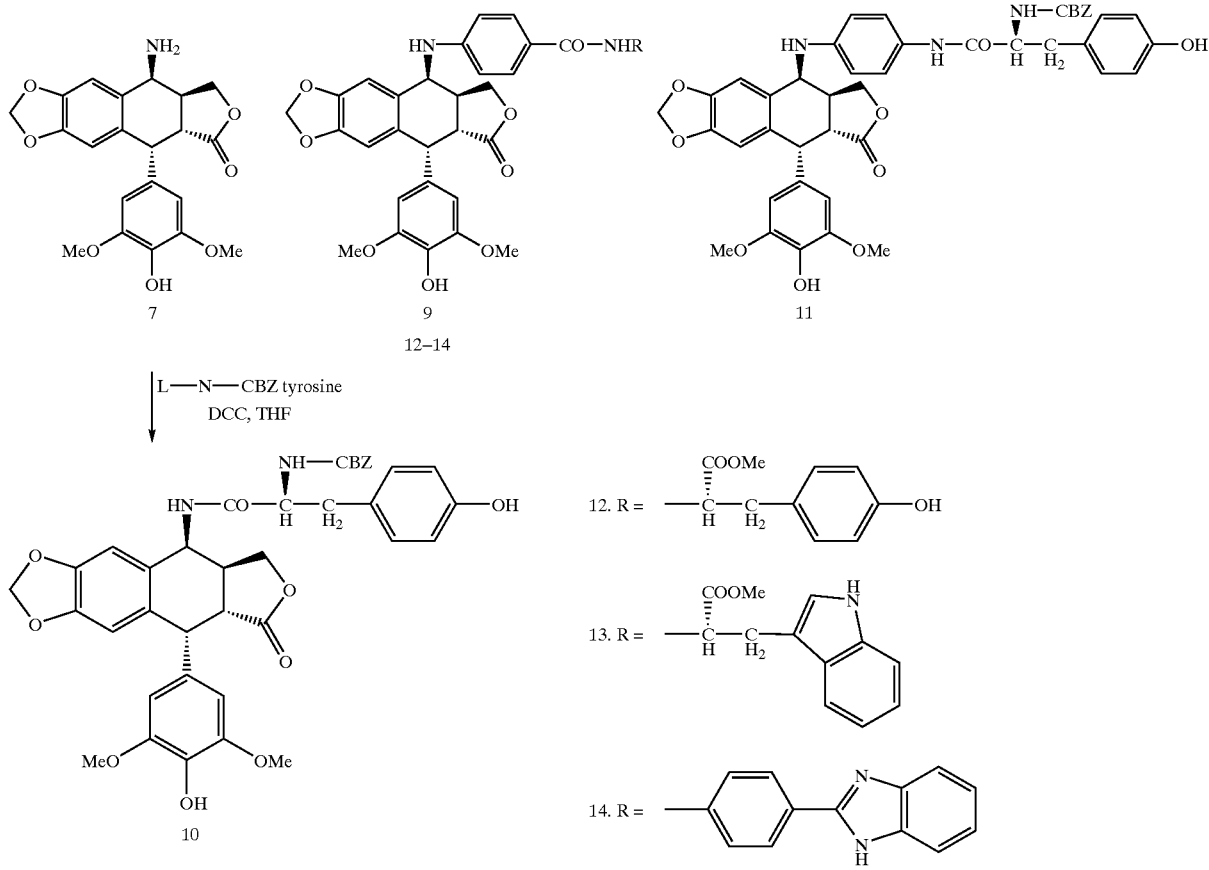

EXAMPLE 2

General Preparation of 4'-demethyl-desoxypodophyllotoxins (10–14). To a solution of an appropriate carbonic acid (0.1 mmol) in tetrahydrofuran (3 ml) was added dicyclohexylcarbodiimide (DCC, 22 mg, 0.11 mmol). After 15 minutes, an appropriate amine (0.1 mmol) was added to the reaction mixture and the mixture was stirred at ambient temperature overnight. The suspension was diluted with 10 ml EtOAc and was filtered. After the solvent was removed under reduced pressure, the crude product was chromatographed on the FlahElute system using a 12M silica cartridge and the elute solvent: EtOAc:hexanes 1:1.

4'-O-demethyl-4β-[(N-CBZ-L-tyrosine-carbonyl)-amino]-4-desoxy-podophyllotoxin (10): yield 80%; mp 155–157° C.; $[\alpha]^{25}_D$ –24.0 (c=0.05, acetone); IR (film) 1745 (lactone), 1735 (amides) 1475, 1450, 1420 (aromatic C=C) cm$^{-1}$; MS m/e: 697 [M+1]$^+$; $^1$H NMR (DMSO) δ9.15 (s, 1 H, —OH), 8.37 (d, J=8.1 Hz, 1H, —NH), 8.23 (s, 1 H, —OH), 7.46 (d, J=7.5 Hz, 1H, —NH), 7.30 (m, 5 H, 2'''–6'''-H), 7.05 (d, J=8.4 Hz, 2 H, 2'',6''-H), 6.65 (d, J=8.4 Hz, 2 H, 3'',5''-H), 6.57 (s, 1 H, 5-H), 6.52 (s, 1 H, 8-H), 6.24 (s, 2 H, 2',6'-H), 5.99 (d, 2 H, —OCH$_2$O—), 5.13 (m, 1 H, 4-H), 4.96 (d, J=5.1 Hz, 2 H, —OCH$_2$—Ph), 4.50 (d, J=5.1 Hz, 1 H, 1-H), 4.19 (t, J=8.1 Hz, 1 H, 11-H), 4.11 (m, 1 H, —CO—CH—N—), 3.85(t, J=8.1 Hz, 1H, 11-H), 3.63 (s, 6 H, 3',5'-OCH$_3$), 3.32 (m, 1 H, 2-H), 2.82 (m, 1 H, 3-H); Anal. (C$_{38}$H$_{36}$N$_2$O$_{11}$·1/2 H$_2$O) C, H, N.

4'-O-demethyl-4β-[(N-CBZ-L-tyrosine-carbonyl)-4''-aminoanilino]-4-desoxypodophyllotoxin (11): yield 48%; mp 192–195° C.; $[\alpha]^{25}_D$ –76.0 (c=0.05, acetone); IR (film) 1738 (lactone, with shoulder) 1475, 1450, 1420 (aromatic C=C) 1216 (phenol) cm$^{-1}$; MS m/e: 787 [M]$^+$; $^1$H NMR (acetone) δ9.01 (s, 1 H, —OH), 7.40 (d, J=8.7 Hz, 2 H, 2''',6'''-H), 7.32 (m, 5 H, 2''''–6''''-H), 7.12(d, J=8.4 Hz, 2 H, 2'',6''-H), 6.82 (s, 1 H, 5-H), 6.75 (d, J=8.4 Hz, 2 H, 3'',5''-H), 6.69 (d, J=8.7 Hz, 2 H, 3''',5'''-H), 6.52 (s, 1 H, 8-H), 6.39 (s, 2 H, 2',6'-H), 5.96 (s, 2 H, —OCH$_2$O—), 5.03 (d, J=6.9 Hz, 2 H, —OCH$_2$—Ph), 4.88 (m, 1 H, 4-H), 4.55 (d, J=4.5 Hz, 1 H, 1-H), 4.41 (m, 1 H, —CO—CH—N—), 4.39 (t, J=8.1 Hz, 1 H, 11-H), 3.91(t, J=8.1 Hz, 1H, 11-H), 3.70 (s, 6 H, 3',5'-OCH$_3$), 3.20 (m, 1 H, 2-H), 2.92 (m, 1 H, 3-H); Anal. (C$_{44}$H$_{41}$N$_3$O$_{11}$·1/2 H$_2$O) C, H, N.

4'-O-demethyl-4β-[4''-(methyl L-tyrosine-N-carbonyl)-anilino]-4-desoxy-podophyllotoxin (12): yield 31%; mp 203° C. (dec.); $[\alpha]^{25}_D$ –183.3 (c=0.03, acetone); IR (film) 1737 (lactone) 1727 (amide and ester) 1462, 1445, 1427 (aromatic C=C) 1217 (phenol) cm$^{-1}$; MS m/e: 696 [M]$^+$; $^1$H NMR (acetone) δ8.38 (s, 1 H, —OH), 7.71 (d, J=8.7 Hz, 2 H, 2''',6'''-H), 7.51 (d, J=8.1 Hz, 1 H, —NH), 7.21 (s, 1 H, —OH), 7.12 (d, J=8.7 Hz, 2 H, 2'',6''-H), 6.82 (s, 1 H, 5-H), 6.75 (d, J=8.7 Hz, 2 H, 3'',5''-H), 6.74 (d, J=8.7 Hz, 2 H, 3''',5'''-H), 6.52 (s, 1 H, 8-H), 6.40 (s, 2 H, 2',6'-H), 5.96 (dd, 2 H, —OCH$_2$O—), 5.03 (m, 1 H, 4-H), 4.80 (m, 1 H, —CO—CH—N—), 4.55 (d, J=4.5 Hz, 1 H, 1-H), 4.39 (t, J=8.1 Hz, 1 H, 11-H), 3.85(t, J=8.1 Hz, 1H, 11-H), 3.70 (s, 6 H, 3',5'-OCH$_3$), 3.23 (m, 1 H, 2-H), 3.05 (m, 1 H, 3-H).

4'-O-demethyl-4β-[4''-(methyl L-tryptophan-N-carbonyl)-anilino]-4-desoxypodophyllotoxin (13): yield 91%; mp 177–179° C. (dec.); $[\alpha]^{25}_D$ –48.0 (c=0.05, acetone); IR (film) 1736 (lactone) 1727 (amide and ester)

1478, 1461, 1433 (aromatic C=C) 1217 (phenol) cm$^{-1}$; MS m/e: 720 [M+1]$^+$; $^1$H NMR (acetone, D$_2$O exchange) δ7.67 (d, J=8.7 Hz, 2 H, 2'",6'"-H), 7.58 (d, J=8.1 Hz, 1 H, 1'"-H), 7.35 (d, J=8.1 Hz, 1 H, 2'"-H), 7.02 (m, 4 H, 4'"-7'" H), 6.77 (s, 1 H, 5-H), 6.73 (d, J=8.7 Hz, 2 H, 3',5'-H), 6.49 (s, 1 H, 8-H), 6.35 (s, 2 H, 2',6'-H), 5.94 (d, 2 H, —OCH$_2$O—), 5.00 (m, 1 H, 4-H), 4.90 (m, 1 H, —CO—CH—N—), 4.54 (d, J=4.8 Hz, 1 H, 1-H), 4.37 (t, J=7.8 Hz, 1 H, 11-H), 3.78(t, J=7.8 Hz, 1H, 11-H), 3.71 (s, 6 H, 3',5'-OCH$_3$), 3.34 (m, 1 H, 2-H), 3.24 (m, 1 H, 3-H).

4'-O-demethyl-4β-{4"-[4'"-(benzimidazol-2""-yl)-amido]-anilino}-4-desoxypodophyllotoxin(14): yield 45%; mp 152–154° C. (dec.); [α]$^{25}_D$–36.0 (c=0.05, acetone); IR (film) 1727 (lactone and amide) 1475, 1455, 1273 (aromatic C=C) cm$^{-1}$; MS m/e: 709 [M–1]$^+$; $^1$H NMR (CDCl$_3$) δ7.52 (d, J=8.7 Hz, 2 H, 2",6"-H), 7.43 (d, J=8.7 Hz, 2 H, 2'",6'"-H), 7.4 (m, 2 H, 4"",7""-H), 6.72 (s, 1 H, 5H), 6.63 (d, J=8.7 Hz, 2 H, 3'",5'"-H), 6.62 (m, 5"",6""-H), 6.54 (s, 1 H, 8-H), 6.53 (d, J=8.6 Hz, 2 H, 3",5"-H), 6.33 (s, 2 H, 2',6'-H), 5.90 (dd, 2 H, —OCH$_2$O—), 4.74 (m, 1 H, 4-H), 4.60 (d, J=4.8 Hz, 1 H, 1-H), 4.37 (t, J=7.8 Hz, 1 H, 11-H), 3.78(m, 1H, 11-H), 3.80 (s, 6 H, 3',5'-OCH$_3$), 3.50 (m, 1 H, 2-H), 3.06 (m, 1 H, 3-H).

EXAMPLE 3

Biological Assay and Results. The compounds 10–14 were evaluated for cell growth inhibition (using the Standard SRB Assay (1990) *J.N.C.I.* 82:1107), cytotoxicity, and in vitro topoisomerase II inhibition as determined using a plasmid relaxation/cleavage assay (Cho et al. (1996) *J. Med. Chem.* 39:1396) using etoposide and GL-331 as standards. The cell growth inhibitory and cytotoxic activities of the target and standard compounds against selected human tumor cell lines are summarized in Table 1. ED$_{50}$ for growth inhibition is the concentration that inhibits 50% cell replication after 3 days of continuous treatment, whereas LD$_{50}$ for cytotoxicity is the concentration that kills 50% of the cells after 30 minutes of treatment. Freshly trypsinized KB cells were exposed to drug at 5, 0.5, or 0.05 μM for 30 minutes, respectively. Then, 250 or 500 cells were immediately plated and left undisturbed for 12 days. Colonies were fixed with formalin and stained with toluidine blue. Compounds 11–13 were superior or comparable to etoposide and GL-331 as inhibitors of tumor cell replication. Unlike etoposide, compounds 11 and 12 exhibited similar profile to GL-331 against MRP-related drug resistant cells (KB-7d). However, compound 11 was not cytotoxic for selected tumor cell lines following short exposure. Compounds 12–14 were further evaluated as cytotoxic agents using clonogenic assays (Table 2). The results show that compounds 12 and 13 (especially 12) were significantly more cytotoxic against KB cells than either GL-331 or etoposide. DNA topoisomerase II inhibitory assays of compounds 12 and 13 showed that linear DNA could be detected after treatment with the drugs (Table 3). Both compounds could induce detectable linear DNA under concentration as low as 5 μM. This shows that 12 and 13 were potent inhibitors of topoisomerase II and are at least as active as GL-331 and four-fold more active than etoposide.

TABLE 1

Cell growth inhibition and cytotoxicity of target and standard compounds against selected human tumor cell lines.*

| Compound No. | Cell growth inhibition ED$_{50}$ (μM) | | | | Cytotoxicity LD$_{50}$ (μM) | | | |
|---|---|---|---|---|---|---|---|---|
| | A549 | MCF-7 | KB | KB-7d (MRP) | A549 | MCF-7 | KB | KB-7d (MRP) |
| Etoposide | 5.2 | >20 | 0.75 | >10 | >50 | 21 | 49.0 | >50 |
| GL-331 | 0.7 | 12.0 | 0.3 | 1.9 | 6.6 | 5.3 | 9.9 | <50 |
| 10 | >20 | — | 2.3 | 6.7 | — | — | — | — |
| 11 | 0.8 | 4.7 | 0.2 | 0.75 | NA | 45 | >10 | >50 |
| 12 | 2.4 | 4.5 | 1.9 | 5 | 12.5 | <3.1 | 1.7 | <20 |
| 13 | — | — | 0.75 | <0.1 | — | — | — | — |
| 14 | — | — | >25 | — | — | — | — | — |

*Cell lines = A549 (lung adenocarcinoma); MCF-7 (breast adenocarcinoma); KB (nasopharyngeal carcinoma) and KB-7d (MRP-pleotrophic multidrug-resistant KB sub-clone)

In summary, five novel epipodophyllotoxin derivatives were designed and synthesized according to the 3D CoMFA models previously constructed. Two compounds (12 and 13) showed superior pre-clinical activities (including cell growth inhibition, cell killing and in vitro topoisomerase II inhibition) as compared to the GL-331 and etoposide prototypes. In addition, compound 12 exhibited a favorable drug-resistance profile similar to that of GL-331.

TABLE 2

Clonogenic assay of compounds 12–14 compared to etoposide and GL-331:

| Compound | Colony Number | % Inhibition |
|---|---|---|
| Control | 110, 98 | — |
| Etoposide(5 μM) | 85, 93 | NA |
| GL-331(5 μM) | 64, 48 | 46% |
| 12(5 μM) | 0, 1 | 99.5% |
| 13(5 μM) | 17, 21 | 82% |
| 14(5 μM) | 105, 93 | NA |

TABLE 3

Relative potency of compounds 12, 13, etposide and GL-331 in DNA topoisomerase II inhibition.

| Compound | Minimum concentration to detect linear DNA ($\mu M$) |
|---|---|
| Etoposide | 20 |
| GL-331 | 5 |
| 12 | 5 |
| 13 | 5 |

The foregoing is illustrative of the present invention, and is not to be construed as limiting thereof. The invention is defined by the following claims, with equivalents of the claims to be included therein.

What is claimed is:

1. A compound according to Formula I:

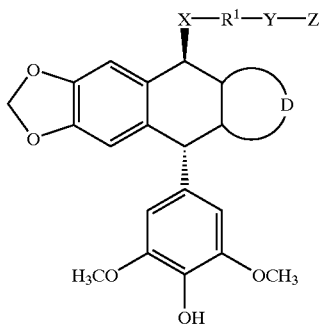

wherein:
X is a linking group selected from the group consisting of —O—, —S—, —NH—, —CO—, —CH=N—, or CH$_2$NH—;
$R^1$ is a covalent linkage between X and Y, or is loweralkyl, loweralkenyl, or phenyl, and when phenyl is unsubstituted or is substituted from one to four times with loweralkyl, hydroxy, alkoxyl, alkylogen, or alkylamino, alkyoxycarbonyl, amino, halogen, nitro, or nitrile;
Y is —NHCO— or —CONH—;
Z is —CHR$_2$—(CH$_2$)$_n$R$_3$, where n is 0 to 2 and R$_2$ is —COOH, —NH$_2$, —COOR$_{31}$ where R$_{31}$ is loweralkyl, COOCH$_2$Ph, or —NHCOOCH$_2$Ph;
R$_3$ is a lower alkyl, loweralkenyl or aryl, which may be unsubstituted or substituted one or more times with loweralkyl, loweralkenyl, or hydroxy, alkoxyl, alkylamino, thioalkyl, hydroxycarbonyl, guanidino, or amido; and
D is selected from the group consisting of —CH$_2$OC(=O)—; —CH$_2$OC(=CH$_2$)—; —CH$_2$CH$_2$C(=O)—; —CH$_2$OC(=S)—; —CH$_2$OCH$_2$—; —CH$_2$OCH(—OH)—; —CH$_2$OCH(OCH$_3$)—; —CH$_2$CH$_2$C(—NR$_{12}$)— where R$_{12}$ is loweralkyl; —C(=O)CH$_2$C(O)—; —CH$_2$OS(=O)(=O)OCH$_2$—; and —CH$_2$OS(=O)OCH$_2$—;
or a pharmaceutically acceptable salt thereof.

2. A compound according to claim 1, wherein X is —NH—.

3. A compound according to claim 1, wherein $R^1$ is phenyl.

4. A compound according to claim 1, wherein $R^3$ is phenyl, indolyl imidazolyl, pyridyl, pyrimidyl, or benzamidazolyl.

5. A compound according to claim 1 having the structure of Formula II:

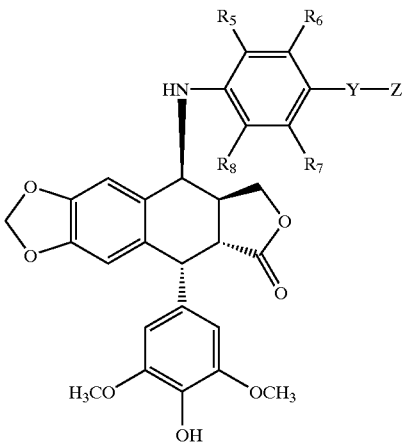

wherein:
Y is an —NHCO— or —CONH— linking group;
Z is —CHR$_2$—(CH$_2$)$_n$R$_3$, where n is 0 to 2 and R$_2$ is —COOH, —NH$_2$, —COOCH$_3$, COOCH$_2$Ph, or —NHCOOCH$_2$Ph;
R$_3$ is a lower alkyl, loweralkenyl or phenyl; and
R$_5$, R$_6$, R$_7$, and R$_8$ are each independently selected from the group consisting of H, loweralkyl, hydroxy, alkoxyl, alkylogen, or alkylamino, alkyoxycarbonyl, amino, halogen, nitro, and nitrile;
or a pharmaceutically acceptable salt thereof.

6. A compound according to claim 1 selected from the group consisting of:
4'-O-demethyl-4β-[(N-CBZ-L-tyrosine-carbonyl)-amino]-4-desoxy-podophyllotoxin (10);
4'-O-demethyl-4β-[(N-CBZ-L-tyrosine-carbonyl)-4"-aminoanilino]-4-desoxypodophyllotoxin (11);
4'-O-demethyl-4β-[4"-(methyl-L-tyrosine-N-carbonyl)-anilino]-4-desoxy-podophyllotoxin (12);
4'-O-demethyl-4β-[4"-(methyl-L-tryptophan-N-carbonyl)-anilino]-4-desoxypodophyllotoxin (13);
4'-O-demethyl-4β-{4"-[4'"-(benzimidazol-2""-yl)-amido]-anilino}-4-desoxypodophyllotoxin (14);
4'-O-demethyl-4β-(methyl L-tyrosyl-N)-4-desoxy-podophyllotoxin;
4'-O-demethyl-4β-{[(4"-hydroxyl-benzenepropanoic methyl ester)-α]-methylamino}-4-desoxy-podophyllotoxin;
4'-O-demethyl-4β-(N-CBZ-L-tyrosyl-C-amino)-4-desoxy-podophyllotoxin;
4'-O-demethyl-4β-(L-tyrosyl-C-amino)-4-desoxy-podophyllotoxin;
4'-O-demethyl-4β-(N-CBZ-L-tyrosyl-C)-4-podophyllol;
4'-O-demethyl-4β-(N-CBZ-L-tyrosyl-C)-4-thio-podophyllol;
4'-O-demethyl-4β-{[4"(N-CBZ-L-tyrosyl-C-amino)]-anilino}-4-desoxypodophyllotoxin;
4'-O-demethyl-4β-{[4"-(methyl L-tyrosyl-N-carbonyl)]-anilino}-4-desoxy-podophyllotoxin;
4'-O-demethyl-4β-{[4"-(methyl L-tryptophanyl-N-carbonyl)]-anilino}-4-desoxypodophyllotoxin;
4'-O-demethyl-4β-{[4"-(methyl L-histidyl-N-carbonyl)]-anilino}-4-desoxypodophyllotoxin;
4'-O-demethyl-4β-{[4"-(L-tryptophanyl-N-carbonyl)]-anilino}-4-desoxypodophyllotoxin;
4'-O-demethyl-4β-{[4"-(methyl D-tryptophanyl-N-carbonyl)]-anilino}-4-desoxypodophyllotoxin;

4'-O-demethyl-4β-(benzyl glycyl-N-carbonyl)-4-desoxypodophyllotoxin;
4'-O-demethyl-4β-(benzyl L-tryptophanyl-N-carbonyl)-4-desoxypodophyllotoxin;
4'-O-demethyl-4β-(benzyl L-tyrosyl-N-carbonyl)-4-desoxypodophyllotoxin;
4'-O-demethyl-4β-(N-CBZ-glycyl-C-methylamino)-4-desoxy-podophyllotoxin;
4'-O-demethyl-4β-(N-CBZ-L-tyrosyl-C-methylamino)-4-desoxy-podophyllotoxin;
4'-O-demethyl-4β-(N-CBZ-L-trptophanyl-C-methylamino)-4-desoxy-podophyllotoxin;
4'-O-demethyl-4β-(methyl L-tyrosyl-N-methylene)-4-desoxy-podophyllotoxin;
4'-O-demethyl-4β-(N-CBZ-L-tyrosyl-C-amino)-4-desoxy-13-methylene-podophyllotoxin;
4'-O-demethyl-4β-(methyl L-tyrosyl-N-carbonyl)-4-desoxy-13-methylene-podophyllotoxin;
4'-O-demethyl-4β-(N-CBZ-L-tyrosyl-C-methylamino)-4-desoxy-13-methylene-podophyllotoxin;
4'-O-demethyl-4β-(N-CBZ-L-tyrosyl-C-amino)-4-desoxy-[2α, 3β]-cyclopentan-13-one-podophyllotoxin;
4'-O-demethyl-4β-(N-CBZ-L-tyrosyl-C-amino)-4-desoxy-13-thio-podophyllotoxin;
4'-O-demethyl-4β-(N-CBZ-L-tyrosyl-C-amino)-4,13-desoxy-podophyllotoxin;
4'-O-demethyl-4β-(N-CBZ-L-tyrosyl-C-amino)-4-desoxy-13-hydroxyl-podophyllotoxin;
4'-O-demethyl-4β-(N-CBZ-L-tyrosyl-C-amino)-4-desoxy-13-methyl ether-podophyllotoxin;
4'-O-demethyl-4β-(N-CBZ-L-tyrosyl-C-amino)-4-desoxy-11,13-O,O'-cyclosulfite-podophyllotoxin; and
4'-O-demethyl-4β-(N-CBZ-L-tyrosyl-C-amino)-4-desoxy-11,13-O,O'-cyclosulfate-podophyllotoxin.

7. A compound according to claim 1 selected from the group consisting of:
4'-O-demethyl-4β-[(N-CBZ-L-tyrosine-carbonyl)-amino]-4-desoxy-podophyllotoxin (10);
4'-O-demethyl-4β-[(N-CBZ-L-tyrosine-carbonyl)-4"-aminoanilino]-4-desoxypodophyllotoxin (11);
4'-O-demethyl-4β-[4"-(methyl-L-tyrosine-N-carbonyl)-anilino]-4-desoxy-podophyllotoxin (12);
4'-O-demethyl-4β-[4"-(methyl-L-tryptophan-N-carbonyl)-anilino]-4-desoxypodophyllotoxin (13); and
4'-O-demethyl-4β-{4"-[4'''-(benzimidazol-2""-yl)-amido]-anilino}-4-desoxypodophyllotoxin (14).

8. A compound according to claim 1 selected from the group consisting of:

4'-O-demethyl-4β-[(N-CBZ-L-tyrosine-carbonyl)-4"-aminoanilino]-4-desoxypodophyllotoxin (11);
4'-O-demethyl-4β-[4"-(methyl-L-tyrosine-N-carbonyl)-anilino]-4-desoxy-podophyllotoxin (12); and
4'-O-demethyl-4β-[4"-(methyl-L-tryptophan-N-carbonyl)-anilino]-4-desoxypodophyllotoxin (13).

9. A compound according to claim 1, wherein said compound is
4'-O-demethyl-4β-[4"-(methyl-L-tyrosine-N-carbonyl)-anilino]-4-desoxy-podophyllotoxin (12).

10. A compound according to claim 1, wherein said compound is
4'-O-demethyl-4β-[4"-(methyl-L-tryptophan-N-carbonyl)-anilino]-4-desoxypodophyllotoxin (13).

11. A pharmaceutical formulation comprising a compound according to claim 1 in a pharmaceutically acceptable carrier.

12. The pharmaceutical formulation according to claim 11, wherein said carrier is an aqueous carrier.

13. A method of treating a cancer, comprising administering to a subject in need thereof a treatment effective amount of a compound according to Formula I:

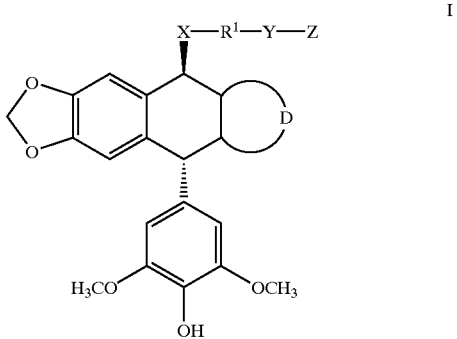

wherein:
X is a linking group selected from the group consisting of —O—, —S—, —NH—, —CO—, —CH=N—, or CH$_2$NH—;
R$^1$ is a covalent linkage between X and Y, or is loweralkyl, loweralkenyl, or phenyl, and when phenyl is unsubstituted or is substituted from one to four times with loweralkyl, hydroxy, alkoxyl, alkylogen, or alkylamino, alkyoxycarbonyl, amino, halogen, nitro, or nitrile;
Y is —NHCO— or —CONH—;
Z is —CHR$_2$—(CH$_2$)$_n$R$_3$, where n is 0 to 2 and R$_2$ is —COOH, —NH$_2$, —COOR$_{31}$ where R$_{31}$ is loweralkyl, COOCH$_2$Ph, or —NHCOOCH$_2$Ph;
R$_3$ is a lower alkyl, loweralkenyl or aryl, which may be unsubstituted or substituted one or more times with loweralkyl, loweralkenyl, or hydroxy, alkoxyl, alkylamino, thioalkyl, hydroxycarbonyl, guanidino, or amido; and
D is selected from the group consisting of —CH$_2$OC(=O)—; —CH$_2$OC(=CH$_2$)—; —CH$_2$CH$_2$C(=O)—; —CH$_2$OC(=S)—; —CH$_2$OCH$_2$—; —CH$_2$OCH(—OH)—; —CH$_2$OCH(OCH$_3$)—; —CH$_2$CH$_2$C(—NR$_{12}$)— where R$_{12}$ is loweralkyl; —C(=O)CH$_2$C(O)—; —CH$_2$OS(=O)(=O)OCH$_2$—; and —CH$_2$OS(=O)OCH$_2$—;
or a pharmaceutically acceptable salt thereof.

14. The method according to claim 13, wherein said cancer is selected from the group consisting of skin cancer, lung cancer, Kaposi's sarcoma, testicular cancer, lymphoma, leukemia, esophageal cancer, stomach cancer, colon cancer, breast cancer, endometrial cancer, ovarian cancer, central nervous system cancer, liver cancer and prostate cancer.

15. The method according to claim 13, wherein said cancer is prostate cancer.

16. The method according to claim 13, wherein said cancer is colon cancer.

17. The method according to claim 13, wherein said cancer is lung cancer.

18. The method according to claim 13, wherein said cancer is breast cancer.

19. The method according to claim 13, wherein X is —NH—.

20. The method according to claim 13, wherein R$^1$ is phenyl.

21. The method according to claim 13, wherein R$^3$ is phenyl, indolyl imidazolyl, pyridyl, pyrimidyl, or benzamidazolyl.

22. The method according to claim 13, said compound of Formula I having the structure of Formula II:

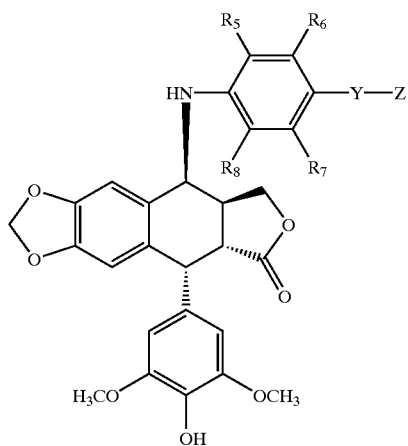

wherein:

Y is an —NHCO— or —CONH— linking group;

Z is —CHR$_2$—(CH$_2$)$_n$R$_3$, where n is 0 to 2 and R$_2$ is —COOH, —NH$_2$, —COOCH$_3$, COOCH$_2$Ph, or —NHCOOCH$_2$Ph;

R$_3$ is a lower alkyl, loweralkenyl or phenyl; and

R$_5$, R$_6$, R$_7$, and R$_8$ are each independently selected from the group consisting of H, loweralkyl, hydroxy, alkoxyl, alkylogen, or alkylamino, alkyoxycarbonyl, amino, halogen, nitro, and nitrile;

or a pharmaceutically acceptable salt thereof.

23. The method according to claim 13, wherein said compound of Formula I is 4'-O-demethyl-4β-[4"-(methyl-L-tyrosine-N-carbonyl)-anilino]-4-desoxy-podophyllotoxin (12).

24. The method according to claim 13, wherein said compound of Formula I is 4'-O-demethy-4β-[4"-(methyl-L-tryptophan-N-carbonyl)-anilino]-4-desoxypodophyllotoxin (13).

25. A compound having the formula:

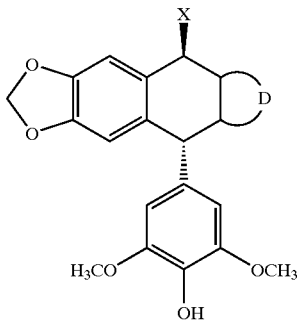

wherein:

X is a linking group selected from the group consisting of —CH=N—, or —CH$_2$NH—; and D is selected from the group consisting of —CH$_2$OC(=CH$_2$)—; —CH$_2$CH$_2$C(=O)—; —CH$_2$OC(=S)—; —CH$_2$CH$_2$C(—NR$_{12}$)— where R$_{12}$ is loweralkyl; —C(=O)CH$_2$C(O)—; and —CH$_2$OS(=O)(=O)OCH$_2$—.

* * * * *